United States Patent [19]

Kuhlmann et al.

[11] 4,322,549

[45] Mar. 30, 1982

[54] OXIDATION OF DI- AND TRIMETHYL AROMATIC HYDROCARBONS HAVING ORTHO-ORIENTED METHYL GROUPS IN LIQUID PHTHALIC ACID

[75] Inventors: George E. Kuhlmann, Lisle; Alan G. Bemis, Naperville, both of Ill.

[73] Assignee: Standard Oil Company (Indiana), Chicago, Ill.

[21] Appl. No.: 874,127

[22] Filed: Feb. 1, 1978

[51] Int. Cl.$^3$ .............................................. C07C 51/16
[52] U.S. Cl. .................................................. 562/416
[58] Field of Search ..................... 260/524 R; 562/416

[56] References Cited

U.S. PATENT DOCUMENTS 3,030,413  4/1962  Taves ................................. 260/524
3,920,735  11/1975  Wampfler et al. .................. 260/524

Primary Examiner—Alan Siegel
Attorney, Agent, or Firm—Fred R. Ahlers; William T. McClain; William H. Magidson

[57] ABSTRACT

Catalytic liquid phase molecular oxygen oxidation of methyl-substituted aromatic hydrocarbons having two or more methyl-substituents on adjacent ring carbon atoms in acetic acid reaction medium have, in general, resulted in a substantial production of the desired ortho-oriented di-, tri-, and higher polycarboxylic substituted aromatic acids but also in the co-production of substantial amounts of oxygenated intermediates including methyl-substituted mono- and non-ortho polycarboxylic acids. Several theories have been proposed, including inherent auto-inhibiton, for such incomplete oxidations.

3 Claims, No Drawings

OXIDATION OF DI- AND TRIMETHYL AROMATIC HYDROCARBONS HAVING ORTHO-ORIENTED METHYL GROUPS IN LIQUID PHTHALIC ACID

STATEMENT OF INVENTION

Such incomplete oxidations of said ortho-methyl oriented aromatics is overcome by conducting their oxidation with a source of molecular oxygen in the presence of liquid o-phthalic acid solution of catalysis provided by a combination of cobalt and manganese as transition metal oxidation catalyst, zirconium, and a source of bromine at a temperature in the range of from 210° C. up to 235° C. and at a pressure above water vapor pressure at such temperature.

It is indeed surprising that the use of o-phthalic acid itself an ortho-oriented dicarboxylic acid and at said reaction temperature range which is below the solidification temperature of the other ortho-tri-, tetra- and higher polycarboxylic substituted aromatics can overcome the prior incomplete oxidations conducted in acetic acid. Because the prior art considered acetic acid to be an excellent reaction solvent for aromatic hydrocarbon feed, a system of catalysis comprising one or more transition metal oxidation catalysts and a source of bromine even for the production of such ortho-oriented di-, tri-, and tetra-, and higher polycarboxylic acids, and partially oxidized intermediate precursor products. Liquid o-phthalic acid is a rather poor solvent for such system of catalysis. Also the analogous preparation of o-phthalic acid in acetic acid reaction solvent from o-xylene suffers the same incomplete oxidation disability mentioned above. Thus, the present oxidation process represents the discovery of unique technical effects providing a substantial technical advance which amount to a novel inventive process.

The essential features of the present inventive oxidation process are: the di-, tri-, tetra- and higher polymethyl substituted aromatic hydrocarbons to be oxidized have at least two ortho-oriented methyl-substituents which when oxidized to carboxylic acid substituents can form an anhydride ring; the system of catalysis consists essentially of the components cobalt and manganese as the transition metal oxidation catalyst, zirconium as the sole non-transition metal and elemental bromine or hydrogen brominde as the source of bromine; the reaction medium is liquid o-phthalic acid (OA) and should be present in the molar range of polyacid to OA not exceeding 2.0:10; the water content of the reaction medium should be at least 3 weight percent but not exceed about 25 weight percent the oxidation temperature is within the range of from 210° C. up to 235° C.; and the oxidation reaction is conducted under pressure which is, as a minimum, just above water vapor pressure at said temperature.

The present inventive process can be conducted in any known manner for carrying out catalytic liquid phase processes; e.g. continuous, batchwise or a continuous mode modified batchwise process. The latter comprises charging all of the reaction medium solution of components of catalysis and 5 to 10% of the di-, tri-, tetra-, or higher polymethyl aromatic hydrocarbons to the oxidation zone, heating the resulting reaction mixture, preferably stirred, to reaction temperature under reaction pressure, introducing air alone for one to five minutes, introducing the remaining methyl-substituted aromatic hydrocarbon feed at a uniform rate with the introduction of air, and at the conclusion of co-introduction of such aromatic hydrocarbon again introducing only air into the oxidation zone until oxygen is no longer being consumed.

SPECIFIC EMBODIMENTS

The di-, tri- and tetra- and higher polymethyl-substituted aromatic feedstocks include such substituted benzenes, biphenyl, terphenyl, and naphthalene as well as benzophenone and benzil. Such substituted benzenes are o-xylene as well as tri-, tetra-, pentamethyl benzenes having two or more ortho-oriented methyl substituents and hexamethyl benzene. Pseudocumene (1,2,4-trimethyl benzene), hemimellitene (1,2,3,5-trimethyl benzene), prenitol (1,2,3,4-tetramethylbenzene), isodurene (1,2,3,5-tetramethyl benzene), and durene (1,2,4,5-tetramethylbenzene) are examples of such tri and tetramethylbenzenes. All of the pentamethylbenzenes as well as hexamethylbenzene qualify as such feedstocks. The methylnaphthalenes which qualify as such feedstocks include 1,2-dimethyl-; 2,3-dimethyl-; 1,2,3-trimethyl-; 1,2,4-trimethyl-; 1,2,5-trimethyl-; 1,2,6-trimethyl-; 1,2,7-trimethyl-; 1,2,8-trimethyl-; 2,3,6-trimethyl-; 2,3,7-trimethyl-; 2,3,8-trimethyl-; 1,2,3,4-tetramethyl-; 1,2,7,8-tetramethyl-; 1,2,6,7-tetramethyl-; 1,2,5,6-tetramethyl-; all the pentamethyl-; hexamethyl-; heptamethyl-; and octamethyl-substituted naphthalenes. Illustrative substituted bi- and terphenyls include 2,3-dimethyl-; 3,4-dimethyl-; 2,2',3'-trimethyl-; 2,3',4-trimethyl-; 3,4,4-trimethyl-; 3,4,5,4'-tetramethyl-; the symetrical tetramethyl-; 2,3,5,3',4'-pentamethyl-; 2,3,4,2',3',4'-hexamethyl-; 2,3,4,5,3',4'-hexamethyl-; the heptamethyl-; the octamethyl-; the monamethyl; and the decamethyl-substituted biphenyls and the like di-, tri-, tetra-, penta-, hexa-, hepta-, octa-, nona-, deca-, hendeca-, dodeca-, tri-eleca-, and tetradeca-methyl-terphenyls and binaphthyls. Of the foregoing feedstocks pseudocumene, sym. di(3,4) biphenyl, durene, 2,3-dimethyl and 2,3,6,7-tetramethylnaphthalene are preferred feedstocks because their di- and tetracarboxylic acids and anhydrides are useful intermediates for the preparation of saturated and unsaturated ester resins from di-, tri- and higher polyols and other acid reactants.

While o-xylene can be oxidized in the presence of o-phthalic acid reaction medium according to the present invention, its zirconium-containing system of catalysis results in excessive combustion of o-xylene to oxides of carbon. The analogous oxidation of o-xylene in liquid o-phthalic acid reaction medium but in the presence of a system of catalysis not employing zirconium is the subject matter of a copending patent application.

For the purposes of this invention its system of catalysis consists for each gram mole of the ortho-oriented di- and higher methyl-substituted aromatics a total 15 milligram atoms of the metals per se and not their salts of zirconium, cobalt and manganese, and from 10 up to 20 milligram atoms of bromine from elemental bromine and/or hydrogen bromide. Preferably the milligram ratio of bromine to total of such metals is 1.0:1.0. It has been found that manganese is the most difficult of the transition catalyst metals to keep in solution as the feedstock (e.g., pseudocumene) is converted to its polycarboxylic acid (e.g., trimellitic acid). For this reason the manganese content of the total of 15 milligram atoms per gram mole of feedstock should not exceed about 6, and is preferably 5 milligram atoms. Suitable Co:Mn:Zr:Br milligram atom ratios are in the range of 5-9:4-6:6-1:10-20. On the foregoing 1:1 ratio of Br:total metals; the milligram atom ratio of Co:Mn:Zr:Br is 5-9:5:5-1:15, and of such ratio range it is most preferred to use for pseudocumene oxidation the milligram atom ratio of 9:5:1:15.

The preference of elemental bromine and/or hydrogen bromide as source of bromine component of the catalysis system is unique for the use of liquid o-phthalic acid as the reaction medium. Although the oxidation of the feedstocks contemplated by this invention will oxidize in the presence of covalent sources of bromines (i.e., organic bromides such as tetrabromoethane) and ionic sources of bromine other than H Br (e.g. NaBr), the use of such other covalent and ionic sources of bromine result in somewhat incomplete oxidations, that is, somewhat high yields of intermediate products; low consumption of oxygen, about 0.3 to 0.7 of the oxygen consumed when $Br_2$ or H Br are used; and highly discolored product acids.

The aromatic polycarboxylic acid products resulting from the feedstocks contemplated for use in this invention have melting points well above 235° C. For example, trimellitic acid product of pseudocumene oxidation melts, under conditions of pressure and concentrations preventing its dehydration to 4-carboxyphthalic anhydride, at a temperature of 252° C. Hence, the oxidation of the contemplated feedstock aromatics in the presence of its liquid product acid would have to be conducted at temperatures above 252° C. which are not feasible for commercial practice.

It is known that the melting point of a chemical compound can be depressed by the addition thereto of another chemical compound. Every potential additive compound does not have the same degree of melting point depressing effect per mole fraction of additive. For example, a mole ratio of one o-phthalic acid to one mole trimellitic acid melts at 210° C. but equal mole ratios of benzene or benzoic acid or trimesic acid and trimellitic acid result in mixtures having melting points above 232° C. Furthermore for equivalent oxidation completion to a mole ratio of about 0.8 mole of o-phthalic acid per mole of trimellitic acid product would, we have determined empirically, require 6.4 moles of acetic acid or 3.3 moles of benzoic acid per mole of tri-mellitic acid product. Thus the selection of liquid o-phthalic acid as the reaction medium for the present inventive process from the many possible reaction media provides not only for the greater oxidation zone capacity for production of the desired aromatic acid product but also provides the unique technical effect of more complete oxidation of feedstock aromatic at lower mole ratios of liquid o-phthalic acid per mole of desired aromatic polycarboxylic acid.

The essential oxidation zone operating pressure for the present invention is defined as a pressure which is, at a minimum, the pressure of water vapor at the operating temperature range of from 210° C. up to 235° C. Because operation below such pressure, water is rapidly removed from the reaction zone by vaporization into the spent air exhaust. Such minimum pressure, 18.4 to 30.2 kg/cm² gauge pressue, is essential to prevent rapid dehydration of both the liquid o-phthalic acid and the desired acid product to their respective intramolecular anhydrides. The preferred operating pressure is 3 to 5 kg/cm² above such minimum gauge pressures. In the absence of such essential non-dehydrating condition, with respect to either the liquid o-phthalic acid reaction medium or the desired aromatic polycarboxylic acid capable of forming an intramolecular anhydride or both, causes rapid deactivation of the catalytic oxidation. Such deactivation, we have also discovered, comes from removal of transition metal oxidation catalyst either from diminishing the metal solubility in the changed reaction medium or by entrapment by the forming anhydride ring or rings or both such dissolution and entrapment.

A minimum concentration of free water, about 3 to 5 weight percent on liquid o-phthalic acid reaction medium is essential for minimum effective solubility of transition metal catalyst components therein. Deactivation of one or more of cobalt and manganese occurs when the water concentration in the liquid reaction medium becomes excessive due to the formation of an inactive geometric configuration specie of metal ion and water. Such inactive specie can be disrupted by supplying extra bromide ion in excess of the 20 milligram atoms per total milligram atom of the three metals but then the enhancing effect of zirconium on rate of oxygen consumption and reaction completion are lost.

Such deactivation of transition metal catalyst component by excess water in the liquid medium in the oxidation is not constant. Rather the deactivation is a technical effect varying with the concentration of oxygen in the liquid phase in the oxidation zone at a selected operating pressure and temperature. Such oxygen concentration can, of course, be increased at a selected operating temperature by increasing the operating pressure. But there is, as a practical matter, with respect to cost of reaction apparatus, a limit to which commercial operating pressure can be increased. A more practical way to increase the oxygen oxidant is to increase the molecular oxygen content in the source thereof supplied to the oxidation zone. For the practice of the present invention, such water concentration deactivation of transition metal catalyst component occurs at above about 15 to 16 weight percent when compressed air (21 Vol. % $O_2$) is supplied to the oxidation zone and above 25-30 weight percent when air fortified with oxygen gas (100 Vol. % $O_2$) is compressed and supplied to said zone. One measure of completeness of the oxidation of the feedstock is the total amount of intermediate oxygenated products produced. Comparative completeness of oxidation then would be the ratio of such total intermediates for a less complete oxidation to the total intermediates for normally, highly complete oxidation. Thus, where unity is assigned to the total intermediates from the normally, highly complete oxidation with air at 13.4 wt. % water concentration in the liquid reaction mixture, air oxidation with air at 16.2% water concentration produces 25-30 times the normal total amount of intermediates but oxidation with air fortified to 50 Vol. % $O_2$ at 19% water concentration produces, within experimental error in determining the amount of each of several intermediates, a total amount of intermediates substantially equivalent to that of the normally, highly complete oxidation. It is preferred for the purposes of this invention to conduct its oxidation of feedstock aromatics with air in the presence of from 7 to 13 weight percent free liquid water in the reaction mixture.

Such preferred concentration of free water in the liquid reaction mixture can be maintained at the oxidation zone temperature of 210°-235° C. and gauge pressure of 21 to 35 kg/cm² by cooling the exhaust (spent air plus water vapor, oxides of carbon, vapors of feed aromatics and oxygenated products thereof) by indirect heat exchange with a coolant so that the temperature of uncondensed portion of the exhaust is not below 118° C. nor above 120° C. at said gauge pressure. The condensate from such cooling of exhaust is returned to the oxidation zone.

A still further essential feature for successful operation of the present inventive process is the mole ratio of aromatic polycarboxylic acid product of the aromatic feedstock to liquid o-phthalic acid reaction medium. Such ratio becomes important only at the maximum which is 2.0 moles of such aromatic polycarboxylic acid per mole of o-phthalic acid. At and above such 2:1 mole ratio the completeness of oxidation of the aromatic feed stock diminishes rapidly at otherwise efficient concentration of catalyst components and operating temperature, pressure and water concentration. Said technical effect can be demonstrated by the oxidation of pseudocumene in the presence of liquid o-phthalic acid under the same efficient conditions of catalyst component concentration, temperature, pressure and water concentration. For such demonstration the mole ratio of trimellitic acid (TMLA) to o-phthalic acid (OA) was varied over the range of 0.27:1.0 to 2.2:1.0 in the oxidations and the percent molar yield of TMLA (% of theory) based on pseudocumene consumed, was determined. The relationship of TMLA molar yield to TMLA:OA molar ratio is shown below in TABLE I.

TABLE I

| Molar ratio TMLA:OA | 0.27:1.0 | 1.2:1.0 | 1.3:1.0 | 1.9:1.0 | 2.2:1.0 |
|---|---|---|---|---|---|
| Molar yield TMLA, % | 82 | 81 | 80 | 77 | 55 |

There is no critical technical effect related to the minimum TMLA:OA molar ratio. Rather the effect is a practical one related to production capacity of the process per unit of oxidation zone volume. For example, since the above establishes that there is no significant decrease in TMLA molar yield over the TMLA:OA molar ratio of from 0.27:1.0 to 1.3:1.0, the practice of the present invention for TMLA production using the TMLA:OA molar ratio of 1.3:1.0 in the reaction zone will produce more than 4.8 times the molar TMLA yield per unit volume of oxidation zone than would be produced from the use of 0.27:1.0 molar ratio of TMLA:OA. The economic thrust of such greater TMLA throughput per unit volume of oxidation zone can be readily recognized as a substantial technical advantage.

While o-phthalic acid per se from o-xylene oxidation is not a preferred main product of the present invention but said xylene is effectively oxidized to OA, it is advantageous for the continuous operation of the present invention to use as the aromatic feedstock a mixture of the polymethyl-substituted precursor of the desired polycarboxylic aromatic acid and o-xylene.

Since o-xylene is the more volatile of the mixture of aromatic feedstocks, its loss by vaporization into the exhaust and even through its non-condensation during exhaust cooling should be taken into account when the molar ratio of polycarboxylic aromatic acid to OA in the oxidation zone exceeds about 1:1., i.e. over the range of 1.2:1.0 up to 1.9:1.0. But from 1:1 down to 0.25:1.0 or lower of such molar ratio the o-xylene vaporization loss is not significant. However, for maintaining such molar ratio of polycarboxylic aromatic acid to OA in the range of from 1.2:1.0 up to 1.9:1.0 the polymethyl aromatic to o-xylene molar ratio need be only 15 to 20 percent greater than such acid product ratio.

For any mode of operation of the present invention wherein both the source of molecular oxygen and ortho-oriented di- and polymethylbenzene are simultaneously introduced into the liquid in the oxidation zone (i.e., semi-continuous or continuous oxidation), the effectiveness of catalysis diminishes when the weight ratio of benzene polycarboxylic acid to water for the liquid reaction mixture in the oxidation zone falls below about 10:1.0. Such lower ratio of benzene polycarboxylic acid to water in the liquid reaction mixture causes the formation of two separate immiscible liquid phases. The top phase contains the aromatic hydrocarbon and the bottom phase contains the benzene di- and polycarboxylic acid products, water, and components of catalysis. Because of the immiscibility of the two phases the oxidation becomes limited to only the interface between the two phases.

The following sealed tube tests illustrate such phase separation. Each of the four compositions below were made in separate heavy walled glass tubes. The tubes were sealed, then heated in an oil both over a range of temperatures from 225° C. to 250° C. and their contents observed. The observation as to color of the heated contents and phases are reported below the contents of each of the four tubes:

TABLE II

| | Tube Number | | | |
|---|---|---|---|---|
| | 1 | 2 | 3 | 4 |
| Contents | Weight % | | | |
| Trimellitic Acid | 40.0 | 46.0 | 19.7 | 53.0 |
| O-Phthalic Acid | 40.0 | 19.7 | 46.0 | 22.7 |
| Cobalt bromide | 0.8 | 1.3 | 1.3 | 1.5 |
| Distilled Water | 3.2 | 6.6 | 6.6 | 7.6 |
| Pseudocumene | 8.0 | 13.2 | 13.2 | 15.2 |
| O-Xylene | 8.0 | 13.2 | 13.2 | 0 |
| Results: | | | | |
| Phases | One | Two | Two | Two |
| Characteristics of phases | Dark Amber Solution | All three had top clear liquid and bottom blue solution. | | |

Evaluation of the above mixtures on the basis of weight ratios of trimellitic acid to o-phthalic acid, pseudocumene (PSC) to water, trimellitic acid to water, and o-phthalic acid to water provides the following information in TABLE III.

TABLE III

| Tube | TMLA/OA | PSC/H$_2$O | TMLA/H$_2$O | OA/H$_2$O |
|---|---|---|---|---|
| 1 | 1:1 | 2.5:1.0 | 12.5:1.0 | 12.5:1.0 |
| 2 | 2.3:1.0 | 2.0:1.0 | 7:1 | 3:1 |
| 3 | 0.43:1.0 | 2.0:1.0 | 3:1 | 7:1 |
| 4 | 2.3:1.0 | 2.0:1.0 | 7:1 | 3:1 |

The formation of two immiscible phases was not from the TMLA/OA yield diminishing ratio of above 2:1, the ratio of PSC to water or the o-phthalic acid to water. Rather the formation of two phases was due to insufficient TMLA to water to make the bottom phase containing TMLA, water and cobalt bromide miscible with the top hydrocarbon phase.

Based on the foregoing evaluations, four semi-continuous air oxidations of pseudocumene were conducted using a mixture of pseudocumene and o-xylene (mole ratio of 0:25:1.0) during the continuous mode of operation to be within the yield diminishing critical limit of TMLA to OA of below 2:1. The same catalysis component ratio to aromatic hydrocarbon water content of liquid reaction mixture, temperatures and pressure are used. But in one oxidation (Run 1) conditions avoiding the formation of two phases are used and in the other oxidations (Runs 2, 3 and 4) three different conditions of aromatic hydrocarbon feed are used to cause formation of the two phases. The duration of the reactions and a partial product composition for the four oxidations are shown below:

TABLE IV

| Example No. | 1 | 2 | 3 | 4 |
|---|---|---|---|---|
| Run duration, Minutes | 94 | 69 | 64 | 65 |
| Partial Products Content: | | All in Grams | | |
| O-Phthalic Acid, grams | 661 | 213 | 204 | 222 |
| Phthalide, grams | 0.3 | 86 | 82 | 81 |
| Trimellitic Acid, grams | 163 | 23 | 22 | 25 |
| Methylphthalic Acids, grams | 0.7 | 89 | 77 | 73 |
| O-Xylene, grams | 0 | 18 | 17 | 15 |
| Pseudocumene, grams | 0 | 8 | 6 | 7 |

The Run Durations were the total time from beginning of reaction until oxygen consumption ceased; that is, exhaust contained 21 Vol. % oxygen on condensible basis. The durations of Runs 2-4 of 69, 64 and 65 minutes, respectively, were due to self-termination caused by the formation of two phases. The substantially identical partial product compositions of Runs 2 to 4 further support their self-terminations and establish that the two phase formation is to be avoided.

Successful practice of the present invention can be monitored by the weight ratio of total hydrocarbon (polymethylbenzene and dimethylbenzene) to water in the condensible portion of the exhaust from the oxidation zone. For such successful operation (avoidance of two phase formation) such hydrocarbon to water weight ratio should be below 1:1 and preferably should be in the range of from 0.4–0.6:1.0. For example, such hydrocarbon to water weight ratio for the above Runs 1–4 are, respectively, 0.6:1.0; 1.0:1.0; 1.43:1.0; and 1.21:1.0.

As stated before the water content of the liquid reaction medium is critical and should be at least 5 weight percent. In three otherwise comparable air co-oxidations of pseudocumene and o-xylene in the molar ratio of 0.25:1.0 conducted at a temperature of 227° C. and a gauge pressure of 28.1 kg/cm² using the same Co:Mn:Zr:Br components of catalysis in the respective milligram atom per gram mole of aromatic hydrocarbon of 5:5:5:15, the temperature of the reflux condenser is varied to change the amount of water condensate returned to the oxidation zone. In each oxidation there is fed 1.0 mole of pseudocumene and 4.0 moles of o-xylene but the unoxidized hydrocarbons trapped from the exhaust after the reflux condenser were not returned to the oxidation zone. Hence the "mole %" yields of OA and TMLA are calculated on the difference between mole fed and mole trapped of the respective methylbenzene. The temperature of the reflux condenser and the results of such co-oxidations are presented in the TABLE V below:

TABLE V

| Example No. | 5 | 6 | Comparative A |
|---|---|---|---|
| Reflux Condenser Temperature | 130° C. | 134° C. | 153° C. |
| Total Product, grams | 744 | 736 | 649 |
| Partial Product Composition: | | | |
| O-Phthalic Acid, grams (mole %) | 471(80) | 454(75) | 356(60) |

TABLE V-continued

| Example No. | 5 | 6 | Comparative A |
|---|---|---|---|
| O-Toluic Acid, grams | 0.6 | 1 | 15 |
| Phthalide, grams | 0.3 | 0.7 | 35 |
| Trimellitic Acid, grams (mole %) | 160(80) | 155(77) | 63(32) |
| Methyl Phthalic Acids, grams | 1 | 0.6 | 33 |
| Water, grams | 93 | 77 | 20 |
| Weight % water in reaction product | 12.5 | 10.5 | 3.1 |

Runs 5 and 6 had respective reaction times of 79 and 84 minutes before oxygen consumption ceased but Comparative A ceased to consume oxygen after 70 minutes. Such shorter reaction was caused by the low water content, 3.1 wt. %, of the liquid reaction medium resulting from loss of water therefrom because the 153° C. temperature of the reflux condenser permitted excessive water vapor to pass through uncondensed and hence not recycled to the reaction zone. Such dehydration of the liquid in the reaction zone, in turn, caused conversion of o-phthalic and trimellitic acids to their anhydrides. During such anhydride formation catalyst metals became trapped as insoluble phthalates or trimellitates. Thus the metals became unavailable for their function in the catalysis system.

By further consideration of the operation differences of the processes of Examples 1 to 4 other reasons for the lack of success of the latter three (premature self-terminating) runs will be noted.

TABLE VI

| Examples No. | 1 | 2 | 3 | 4 |
|---|---|---|---|---|
| Aromatic hydrocarbon pump; | | | | |
| on, min. | 5 | 25 | 24 | 34 |
| off, min. | 50 | 69 | 64 | 65 |
| Temperature of uncondensed materials, °C. | 120 | 102 | 120 | 113 |

In the above tabulated operations the on time for aromatic hydrocarbon pumping is the time in minutes from the start of the oxidation. Runs 2 to 4 ceased when aromatic hydrocarbon pumping ceased. Thus the start of hydrocarbon pumping was too late. In a run similar to Run 1, but with hydrocarbon pumping (on) started at the fifteenth minute of operation and continued until the sixty-fourth minute (off) of the operation, the oxidation reaction was self-terminating (oxidation ceased) at said sixty-fourth minute. This supports the conclusion reached with respect to Runs 2 to 4. Thus for more complete oxidation under such semi-continuous operation the introduction of the additional di- or trimethylbenzene into the oxidation zone should be started before the oxidation therein has been in progress more than 10 minutes and preferably such introduction of additional di- or trimethylbenzene should be started from the first to the tenth minute from initiation of oxidation. Also such addition of di- or trimethylbenzene should be concluded by the fortieth to fiftieth minute after oxidation initiation.

Four continuous hydrocarbon feed modified batchwise co-oxidations of o-xylene and pseudocumene are conducted at 28 kg/cm² gauge pressure in the presence of cobalt, manganese, zirconium and bromine (provided by HBr) in the respective Co:Mn:Zr:Br milligram atom per gram mole of total aromatic hydrocarbon charged of 5:5:5:15 solubilized by the presence of 30 milligram mole o-toluic acid per gram mole of hydrocarbon. The reflux condenser was cooled with 153° C. temperature steam which provided uncondensed gas-vapor discharge mixture having a temperature of 120°–121° C. to maintain the water content in the oxidation zone liquid within the 3 to 6 weight percent range. The pumping of indicated hydrocarbon(s) is started in each case 5 minutes after initiation of oxidation and stopped 50 minutes after oxidation initiation. The operating temperatures, amounts of each aromatic hydrocarbon charged, evaporated and not returned to the oxidation and net oxidized; and amounts of products and co-products are shown in TABLE VI to follow:

TABLE VI

| Co-Oxidation of Pseudocumene and Ortho-xylene at 28 kg/cm² Gauge Pressure | | | | |
|---|---|---|---|---|
| Example No. | 7 | 8 | 9 | 10 |
| Operating Conditions: | | | | |
| Temperature: | | | | |
| Initiate, °C. | 160 | 160 | 160 | 160 |
| Range, °C. | 225–229 | 225–229 | 226–228 | 226–228 |
| Average, °C. | 228 | 228 | 226.7 | 227 |
| Total Hydrocarbon Charged: | | | | |
| O—Xylene, gram mole | 6.66 | 7.11 | 6.11 | 5.15 |
| Pseudocumene, gram mole | 1.00 | 0.49 | 1.49 | 2.22 |
| Hydrocarbon pumped: | | | | |
| O—Xylene, mole | 2.52 | 1.96 | 1.96 | 0 |
| Pseudocumene, mole | 0 | 0.49 | 0.49 | 2.22 |
| Run time, min. | 94 | 89 | 100 | 104 |
| Total Hydrocarbon Vaporized and Not Returned: | | | | |
| O—Xylene, gram mole | 2.34 | 2.25 | 2.50 | 1.79 |
| Psuedocumene, gram mole | 0.10 | 0.13 | 0.12 | 0.71 |
| Net Oxidizate: | | | | |
| O—Xylene, gram mole | 4.32 | 4.86 | 3.61 | 3.36 |
| Pseudocumene, gram mole | 0.90 | 0.36 | 1.37 | 1.29 |
| Partial Product Yields, grams: | | | | |
| O—Phthalic Acid (mole %) | 661(92) | 745(92) | 570(95) | 542(97) |
| O—Toluic Acid | 2.0 | 0.1 | 0.7 | 1.0 |
| 2-Carboxybenzaldehyde | 6.0 | 11.0 | 23.0 | — |
| Benzoic Acid | 16.0 | 7.0 | 5.0 | 5.0 |
| Phthalide | 0.3 | 0.3 | 3.0 | 3.0 |
| Trimellitic Acid (mole %) | 163(86) | 61(81) | 225(78) | 222(82) |

TABLE VI-continued

| Co-Oxidation of Pseudocumene and Ortho-xylene at 28 kg/cm² Gauge Pressure | | | | |
|---|---|---|---|---|
| Example No. | 7 | 8 | 9 | 10 |
| Methylphthalic Acids | 0.7 | 0.1 | 3.0 | 5.0 |

The results of six (five illustrative and one comparative) co-oxidations of o-xylene and pseudocumene are given in TABLE VII to follow. All six oxidations are conducted batchwise, that is, all cobalt and hydrocarbons are charged, stirred and heated to initiation temperature before air is injected into the heated, stirred liquid. The six oxidations are conducted at 28 kg/cm² in the presence per gram mole of total hydrocarbon of Co, Mn, Zr, and Br in the milligram atom ratio of 5:5:5:15 with 30 milligram mole of o-toluic acid to solubilize the metal components in the aromatic hydrocarbon.

TABLE VII

| Example No. | 11 | 12 | 13 | 14 | 15 | Comparative B |
|---|---|---|---|---|---|---|
| Temp.: | | | | | | |
| Initiate, °C. | 168 | 160 | 160 | 160 | 160 | 160 |
| Range, °C. | 221–231 | 233–227 | 221–228 | 217–226 | 226–228 | 225–228 |
| Average, °C. | 225 | 225 | 226.5 | 225 | 227 | 226.5 |
| Run Time, Min. | 85 | 92 | 79 | 92 | 90 | 102 |
| Hydrocarbon Charged: | | | | | | |
| O—Xylene, gm. mole | 2.36 | 2.36 | 4.0 | 2.5 | 2.5 | 1.0 |
| Psuudocumeme, gm. mole | 2.5 | 2.5 | 1.0 | 2.5 | 2.5 | 4.0 |
| Hydrocarbon Vaporized and Not Returned: | | | | | | |
| O—Xylene, mole | 0.81 | 0.76 | 0.83 | 0.83 | 0.98 | 0.21 |
| Pseudocumene, mole | 0.44 | 0.30 | 0.08 | 0.62 | 0.42 | 1.07 |
| Net Oxidizate: | | | | | | |
| O—Xylene, mole | 1.55 | 1.60 | 3.17 | 1.67 | 1.52 | 0.79 |
| Pseudocumene, mole | 2.06 | 2.20 | 0.92 | 1.88 | 2.08 | 2.93 |
| Partial Products, gms (mole %): | | | | | | |
| O—Phthalic Acid | 232(90) | 238(93) | 471(89) | 258(93) | 243(96) | 88(67) |
| O—Toluic Acid | 0.5 | 0.5 | 0.6 | 0.5 | 0.4 | 0.6 |
| Phthalide | 0.2 | 0.2 | 0.3 | 0.2 | N.D.* | 8 |
| 2-Carboxybenzaldehyde | 5 | 5 | 8 | 6 | 4 | 44 |
| Benzoic Acid | 2 | 3 | 3 | 3 | 2 | 0.7 |
| Trimellitic Acid | 343(79) | 352(76) | 160(83) | 360(90) | 358(82) | 247(40) |
| Methylphthalic Acids | 5 | 0.5 | 1 | 1 | 2 | 187 |

*None Detected

In all the foregoing and following examples, both illustrative and comparative, the air feed rates were 5 liters of air per minute per liter of liquid hydrocarbon.

COMPARATIVE OXIDATION C

A batchwise oxidation is conducted as in Example 11–15 but at 42 kg/cm² gauge pressure, initiated at a temperature of 160° C. but operated within the temperature range of 243°–250° C. and average of 248° C. temperature using 4.41 moles of pseudocumene and no o-xylene with Co, Mn, Zr and Br catalysis at the milligram atom ratio of Co:Mn:Zr:Br of 5.7:5.7:5.7:7.17 per gram mole of pseudocumene. The catalyst metals were solubilized with 0.33 milligram mole of o-toluic acid per gram mole pseudocumene. During the 78 minutes oxidation 1.33 gram mole of pseudocumene are vaporized from, and not returned to the oxidation zone. Of the 3.08 gram moles of pseudocumene oxidized the 283 grams of trimellitic acid produced is only a 43.8 mole percent yield contaminated with 127 grams of methylphthalic acids which amount to 44.5% of the trimellitic acid produced. Such a solventless oxidation reaction is of little value.

Each of the co-produced benezene di- and tri-carboxylic acids as its anhydride has in its own rights been a long established, desired commercial product. However, the anhydride of the o-phthalic acid is in much greater demand than trimellitic anhydride. But such imbalance of phthalic anhydride to trimellitic anhydride commercial demand is most favorable for the conduct of the present inventive co-oxidation process. The reaction product of the present inventive co-oxidation process can be readily separated into the two different anhydrides by first heating said reaction product to convert its benzene di- and tricarboxylic acids to their anhydrides thereby also vaporizing the anhydrides, and separately condensing the vaporized anhydrides as individual partially purified anhydrides for their final purification by fractional distillation.

The present invention has been described in detail and with reference to specific embodiments thereof to enable those skilled in this art to practice the present invention either as illustrated and/or so understand it, that such skilled person can make the apparent modifications and changes required to practice the invention in other manners within its spirit and scope to fit selected design and operating needs not so illustrated.

What is claimed is:

1. The method of co-oxidizing o-xylene and pseudocumene with air or air enriched with oxygen gas to a mixture containing up to 50 volume percent oxygen in the absence of added extraneous reaction solvent or medium which comprises conducting the oxidation in the presence of from 3 up to 23 weight percent free liquid water; under liquid phase conditions at a temperature in the range of from 210° C. up to 235° C.; under a gauge pressure of from 3 to 5 kg/cm$^2$ above the vapor pressure of water at said temperature; in the presence of catalysis for each 1.0 gram mole of aromatic hydrocarbon of 5 to 9 milligram atom of cobalt, 4 to 6 milligram atoms of manganese, 6 to 1 milligram atoms of zirconium, and 10 to 20 milligram atoms of bromine provided by elemental bromine or hydrogen bromide, wherein initial retention of ions of said metals in solution is aided by from 10 up to 30 milligram moles of o-toluic acid per gram mole of aromatic hydrocarbon; and the ratio of pseudocumene to o-xylene charged to the oxidation is such that the mole ratio of trimellitic acid to o-phthalic acid in the reaction mixture does not exceed 2:1.

2. The co-oxidation method of claim 1 wherein the ratio of pseudocumene to o-xylene is such that the mole ratio of trimellitic acid to o-phthalic acid in the reaction mixture is in the range of from 0.27:1.0 up to 1.3:1.0.

3. The method of claim 2 conducted in a modified batchwise operation comprising a first mode wherein all the components of catalysis and its metal component solubilizing aid and a minor portion of one or both of the aromatic hydrocarbons are charged and oxidized with air starting at a temperature of 160°–170° C. for 5 to 15 minutes, thereafter conducting the oxidation by a continuous mode whereby the remaining aromatic hydrocarbon to be used and air are continuously and simultaneously added to the liquid reaction mixture for a period of time not exceeding 50 minutes, and then charging only air to the liquid reaction mixture until consumption of oxygen essentially ceases and then discharging the resulting reaction mixture for recovery of trimellitic acid and o-phthalic acid as their separate anhydride products.

* * * * *

UNITED STATES PATENT OFFICE
CERTIFICATE OF CORRECTION

Patent No. 4,322,549            Dated March 30, 1982

Inventor(s) George E. Kuhlmann and Alan G. Bemis

It is certified that error appears in the above-identified patent and that said Letters Patent are hereby corrected as shown below:

| Col. | Line | |
|---|---|---|
| 1 | 47 | "brominde" should be --bromine-- |
| 1 | 52 | "percent the oxidation" should be --percent; the oxidation-- |
| 2 | 32 | "symetrical" should be --symmetrical-- |
| 3 | 59 | "cause operation" should be --cause of operation-- |
| 4 | 52 | "air oxidation with air" should be --oxidation with air-- |
| 6 | 23 | "oil both" should be --oil bath-- |

Table VII    "Psuudocumene" should be --Pseudocumene--
Under Example No.
9 lines down Signed and Sealed this Fifth Day of October 1982

[SEAL]

Attest:

GERALD J. MOSSINGHOFF

Attesting Officer     Commissioner of Patents and Trademarks